United States Patent [19]

Vartiainen

[11] Patent Number: 5,893,197
[45] Date of Patent: Apr. 13, 1999

[54] METHOD FOR THE SHAPING OF FIBRES WITH ASSISTANCE OF ELECTRIC CHARGE

[75] Inventor: Kent Vartiainen, Lerum, Sweden

[73] Assignee: SCA Mölnlycke AB, Gothenburg, Sweden

[21] Appl. No.: 08/836,823
[22] PCT Filed: Dec. 8, 1995
[86] PCT No.: PCT/SE95/01485
§ 371 Date: Jun. 4, 1997
§ 102(e) Date: Jun. 4, 1997
[87] PCT Pub. No.: WO96/17568
PCT Pub. Date: Jun. 13, 1996

[30] Foreign Application Priority Data

Dec. 9, 1994 [SE] Sweden .................. 9404287

[51] Int. Cl.⁶ ........................................... D01G 25/00
[52] U.S. Cl. ................................ 19/301; 19/296; 19/304
[58] Field of Search .................. 19/296, 297, 298, 19/299, 300, 301, 302, 303, 304; 264/435, 436

[56] References Cited

U.S. PATENT DOCUMENTS

| | | | |
|---|---|---|---|
| 4,208,366 | 6/1980 | Kinney | 19/296 |
| 4,284,595 | 8/1981 | Peters et al. | 19/296 |
| 4,430,372 | 2/1984 | Knoke et al. | 428/90 |
| 4,432,916 | 2/1984 | Logan | 19/296 |
| 5,161,283 | 11/1992 | Hansen | 19/296 |
| 5,196,212 | 3/1993 | Knoblach | 19/296 |
| 5,382,609 | 1/1995 | Lock | 19/296 |

FOREIGN PATENT DOCUMENTS 0010756  5/1980  European Pat. Off. .......... 19/296

Primary Examiner—Diana L. Biefeld
Assistant Examiner—Larry D. Worrell, Jr.
Attorney, Agent, or Firm—Burns, Doane, Swecker & Mathis, L.L.P.

[57] ABSTRACT

A method for manufacturing an absorbent structure in an absorbent product such as a sanitary napkin, panty liner, diaper or similar product, which is manufactured by air-permeable forming elements. In the present method, the constituent fibres or similar material are given a certain electrical potential while the forming elements completely or partially are given an opposite potential or are grounded, the position and duration of the potential being variable. The material's orientation, distribution and location can be controlled so that the structure in the absorbent product can have the desired appearance.

17 Claims, 2 Drawing Sheets

1  2  3

_5,893,197_

METHOD FOR THE SHAPING OF FIBRES WITH ASSISTANCE OF ELECTRIC CHARGE

BACKGROUND

The present invention concerns a method for the manufacture of an absorbing structure in an absorbent product, such as a sanitary napkin, panty liner, incontinence protector, diaper or similar article, which is manufactured by means of air-permeable shaping elements, combined with the use of electric potential differences.

TECHNICAL BACKGROUND

Many different designs of such absorbent products are known. The absorption body in such products is conventionally produced by dry defibrating cellulose pulp in the form of rolls, bales or sheets, and converting it in fluffed-up form into a pulp web, sometimes with the inclusion of so-called super absorbents, that is, polymers with the capacity to absorb several times their own weight of water or body fluids.

Pulp cores are often compressed, partly to increase their wicking ability, and partly to reduce the bulk of the pulp core to achieve a product which is as compact as possible.

The absorption body can also include other components which can, for example, increase its wicking ability as well as increase its resistance to deformation during use. An example of such components is cellulose fibres which are stiffened by chemical or other means. Other examples of such components are different types of connecting fibres.

A problem which occurs during the manufacture of these products is that current methods for forming webs of individual absorption structures are complicated. They are also limiting in speed, and limit the ability to manufacture more complicated absorption structures having multiple layers and with admixture of different types of for example super absorbents, connecting fibres or such like.

In connection with this technical field, it is usual to use suction to fill moulds on a so-called web former with absorbent material by supplying the mould with a mixture of air and absorbent material, whereby the air flows through the air-permeable surfaces and leaves behind its load of absorbent material. As the layers of deposited material are in themselves air-permeable, successive layers of material can be laid down until the moulds are filled. WO-A-90 05511 and EP 155 752 show two arrangements which use such a method and which include such moulds. These arrangement further show rotating brush means for the removal of surplus absorbent material which lies above the top level of the mould.

U.S. Pat. No. 4,675,144 shows an alternative arrangement for manufacturing an absorption body, whereby a web of fibres is built up on an endless air-permeable belt, called a wire cloth, in a manner similar to that described above. Absorption bodies are then cut out from the built-up fibre web.

Further, EP 0,010,756 shows a process for manufacturing a non-woven material, whereby the fibres are given an electrical charge when they pass between two rollers between which an electrostatic field is present. The fibres are subsequently collected on a moving collector surface.

TECHNICAL PROBLEM

One problem with manufacturing the above-mentioned products by means of such arrangements or similar arrangements is the difficulty of controlling the distribution in the absorption body of the fibres or other absorption materials, such as polyacrylate, CMC, etc. This difficulty can lead to undesirable density and thickness variations in the absorption body. Furthermore, there is no control over the orientation that each fibre takes up in the absorption body which leads to disadvantages such as uncontrolled directions of flow, poor tensile strength in varying directions as well as reduced absorption capacity.

BRIEF DESCRIPTION OF THE INVENTION

The problem of controlling the material distribution and orientation is solved in the present invention by giving such materials, before they arrive at the web former, a powerful electrical charge by means of an electrostatic field which is generated as the material arrives, for example by means of rotating wheels, a grid or similar means. Grounding the web former moulds, either partially or wholly, produces potential differences which can be used to control the placement of the materials.

By giving different materials different potentials, it is also possible to arrange the three-dimensional distribution of the different materials, which in turn leads to several advantages in connection with flow speed and direction. A further advantage with the present invention is that the presence of air-born dust in the vicinity of the production machine is reduced.

DETAILED DESCRIPTION OF THE INVENTION

The inventive method is based upon the well known fact that elements with different electro-magnetic potentials are attracted to one another. It is also known that the bigger the difference in potential between the two elements, the bigger the attractive force which occurs between said elements. In the method according to the present invention, one element or several elements lying beside or after one another, are located under the web former. Said elements can even form different kinds of patterns, and possibly said elements can even be part of the web former itself. These elements are then given a determined polarity, preferably by grounding. In a preferred embodiment, the base and possibly also the sides of the web former are in the form of a so-called lattice, that is a plurality of small discrete elements which can have their potentials controlled separately, for example by means of a PC. Fibres or comparable material which are fed into the web former via one or more feed ducts are given a charge which can be varied in strength and which is opposite that on the above-named elements. By varying the extension in time and space of the ground elements, and by varying the charge on the fibres or comparable materials, it is possible to achieve a great variety of fibre distributions and orientations. Furthermore, it is possible to control the placement of the fibres or similar material in yet another plane, the vertical plane, by the use of materials such as polar fibre types etc., or fibres which have been made polar by a suitable treatment such as, for example, water coating.

Figure 1:
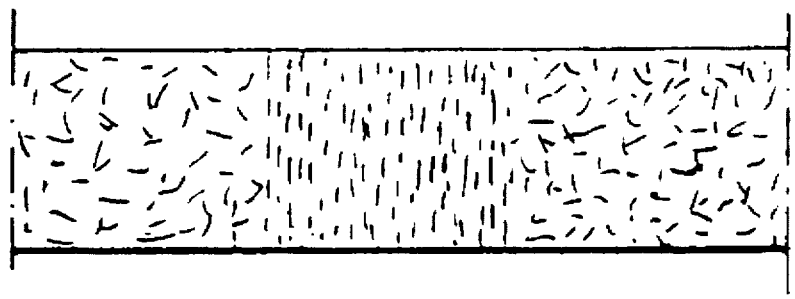
FIG. 1 shows a cross-sectional view from the side of a part of an absorption body, in which a region of the absorption body contains "standing" fibres which positively influence the flow of liquids in the vertical direction.
Figure 2:
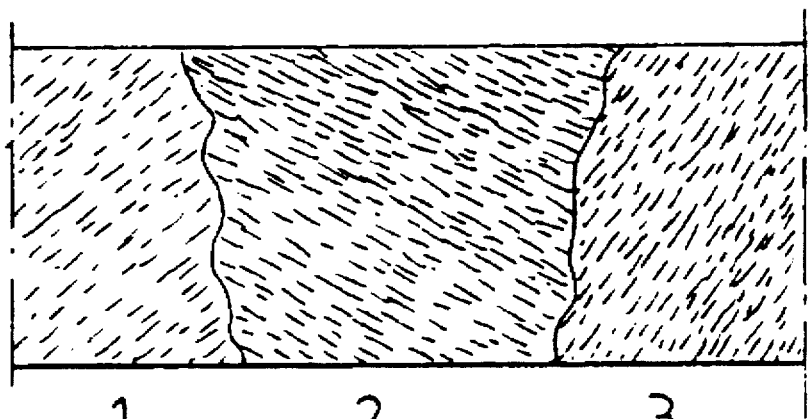
FIG. 2 shows part of an absorption body seen from above, in which sections through various planes in the body are visible in order to illustrate the orientation of the fibres in the different planes 1, 2 and 3. The orientation of the fibres are similar to that of wood fibres in a so-called plywood sheet, and in this way high strength is achieved.
Figure 3:
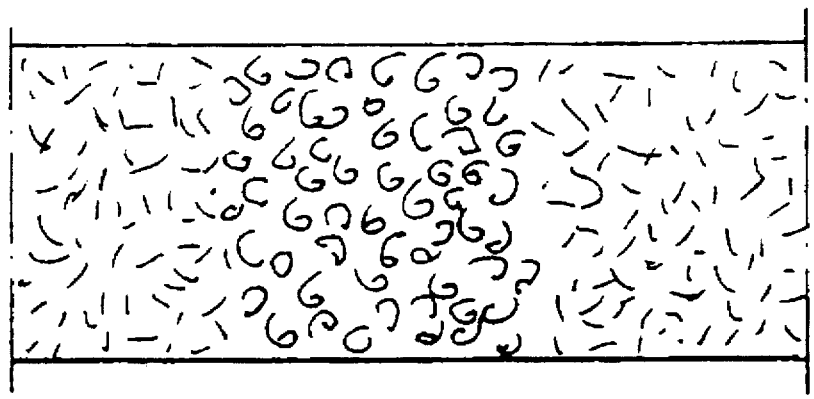
FIG. 3 shows part of an absorption body seen from above/from the side, to illustrate the possibility to control the exact location of a type of fibre within the absorption body.
Figure 4:
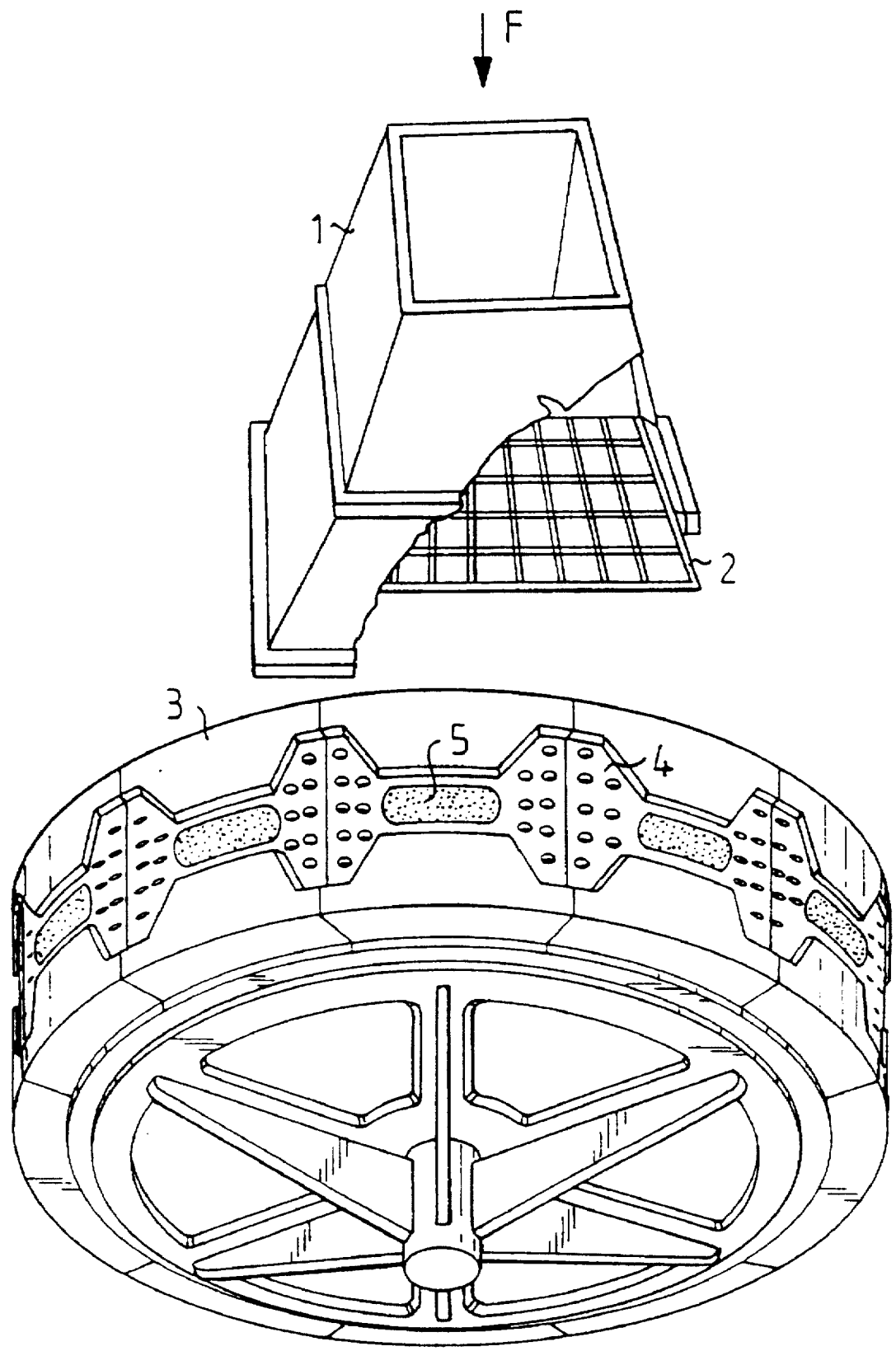
FIG. 4 shows a web former wheel with the accompanying web former hood, and a device for charging the absorbent material. Further, there is shown a zone, preferably grounded, located in the web former moulds.

In a pre-erred embodiment, the material which is to form the absorption body is charged to a potential when it is being introduced into the web forming area. The potential can vary from between 0.1 kV to 100 kV depending on particle size, material, manufacturing speed, etc. Under certain conditions, the potential can go up to 150–200 kV. FIG. 4 shows a web former hood 1 and a web former wheel 3. Fibres supplied to the web former hood 1 are indicated by the arrow F. In this preferred embodiment, the material is given the desired potential by passing the material through a grid 2 of electrodes which are supplied by a high-voltage generator. Furthermore, some parts 5 of the web former moulds 4 located in the web former wheel 3 are grounded, other parts are insulated, and further parts are connected to another generator which can bring about a variable potential opposite to that produced by the first generator. In this way, the desired control of the material is brought about.

We claim:

1. A method for the manufacture of an absorbent structure in an absorbent product from one or more constituent materials, said method comprising:

depositing a constituent material, from a mixture of air and said material, on an air-permeable forming element while drawing air through the forming element so as to form the absorbent structure thereon, controlling the depositing step to obtain selective orientation, distribution and placement of the constituent material throughout the absorbent structure, said controlling step including electrically charging the constituent material before it reaches the forming element, creating an electric field adjacent the forming element, and thus creating potential differences between the constituent material and the electric field adjacent the forming element such that selective orientation, distribution and placement of the constituent material is obtained.

2. A method according to claim 1, wherein the potential differences are brought about by grounded control elements placed under the forming element.

3. A method according to claim 1, wherein the potential differences are brought about by grounded control elements which are at least partially constituted by the forming element itself.

4. A method according to claim 2, wherein the potential differences are brought about by varying the potentials over a period of time.

5. A method according to claim 1 wherein different constituent materials are deposited on the forming element, said charging step including charging the different materials to different potentials.

6. A method according to claim 1, further comprising varying the charge on the constituent material.

7. A method according to claim 3 wherein the constituent materials are fed to the forming elements by one or more nozzles, whereby the constituent materials are given an electrical charge by means of a charging means, placed in said one or more nozzles.

8. A method according to claim 7, wherein the constituent materials are materials which have with respect to each other different conductivity, size and shape.

9. A method according to claim 1, wherein the constituent materials are selected from the group consisting of cellulose fibres, super absorbents, CMC, poly-acrylates and non-absorbing connecting fibres.

10. A method according to claim 6, wherein one or more of the constituent materials is polar.

11. A method according to claim 7, wherein said control elements form a pattern which corresponds to the desired material distribution in the absorbent structure.

12. A method according to claim 11, wherein said control element forms a lattice made up of many small discrete elements, and the potential of each small discrete element is individually controlled.

13. A method according to claim 12, further including electronically controlling the charge distribution for the lattice and for the charging means placed in the nozzles.

14. A method according to claim 13, wherein said electronically controlling step includes using a PC.

15. A method according to claim 1, wherein said electric field creating step includes creating a selective variation of the electric field within a boundary of the forming element.

16. A method according to claim 1, wherein the potential differences are brought about by control elements of selective potential.

17. A method according to claim 1, wherein the potential differences are brought about by control elements of selective potential which are at least partially constituted by the forming element itself.

* * * * *